United States Patent
Reiter et al.

(10) Patent No.: US 9,732,327 B2
(45) Date of Patent: Aug. 15, 2017

(54) FORMULATION OF SUGAR SOLUTIONS FOR CONTINUOUS ULTRACENTRIFUGATION FOR VIRUS PURIFICATION

(71) Applicants: BAXALTA INCORPORATED, Bannockburn, IL (US); BAXALTA GMBH, Glattpark (Opfikon) (CH)

(72) Inventors: Manfred Reiter, Vienna (AT); Leopold Grillberger, Vienna (AT); Wolfgang Mundt, Vienna (AT); Artur Mitterer, Orth/Donau (AT); Horst Schafhauser, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 14/604,018

(22) Filed: Jan. 23, 2015

(65) Prior Publication Data
US 2016/0060603 A1    Mar. 3, 2016

Related U.S. Application Data

(63) Continuation of application No. 12/112,191, filed on Apr. 30, 2008, now Pat. No. 8,969,533.
(Continued)

(51) Int. Cl.
*C12N 7/00* (2006.01)
*A61K 39/145* (2006.01)
(Continued)

(52) U.S. Cl.
CPC ............... *C12N 7/00* (2013.01); *A61K 39/12* (2013.01); *A61K 39/145* (2013.01); *A61K 39/00* (2013.01);
(Continued)

(58) Field of Classification Search
None
See application file for complete search history.

(56) References Cited

U.S. PATENT DOCUMENTS

| | | | |
|---|---|---|---|
| 4,158,054 A | 6/1979 | Furminger et al. |
| 4,217,418 A | 8/1980 | McAleer et al. |

FOREIGN PATENT DOCUMENTS

| | | | |
|---|---|---|---|
| CN | 1739801 A | 3/2006 |
| EP | 0005408 A2 | 11/1979 |

(Continued)

OTHER PUBLICATIONS

Nettleton and Rweyemamu, "The Association of Calf Serum with the Contamination of BltK21 Clone 13 Suspension Cells by a Parvovirus Serologically Related to the Minute Virus of Mice (MVM)" Arch. Virol. 1980; 64: 359-374.*

(Continued)

*Primary Examiner* — Janet L Andres
*Assistant Examiner* — Stuart W Snyder
(74) *Attorney, Agent, or Firm* — Troutman Sanders LLP

(57) ABSTRACT

The present invention provides a method for purification of a virus or virus antigen comprising providing a virus preparation and centrifugation of said virus preparation in a gradient of a sugar established by the addition of two or more buffered sugar layers of different concentration. The method leads to higher yields and reduces unwanted aggregation of the virus or virus antigen by increasing the volume of the peak pool.

27 Claims, 1 Drawing Sheet

Related U.S. Application Data

(60) Provisional application No. 60/927,692, filed on May 4, 2007.

(51) Int. Cl.
*A61K 39/12* (2006.01)
*A61K 39/00* (2006.01)

(52) U.S. Cl.
CPC .............. *C12N 2750/14351* (2013.01); *C12N 2760/16134* (2013.01); *C12N 2760/16151* (2013.01); *C12N 2760/16152* (2013.01); *C12N 2760/16234* (2013.01); *C12N 2760/16251* (2013.01); *C12N 2760/16252* (2013.01)

(56) References Cited

FOREIGN PATENT DOCUMENTS

| | | |
|---|---|---|
| JP | 54154517 A | 12/1979 |
| JP | H06247995 A | 9/1994 |
| JP | 2007068401 A | 3/2007 |
| WO | 2004087760 A1 | 10/2004 |

OTHER PUBLICATIONS

Brakke, Dispersion of aggregated barley stripe mosaic virus by detergents, *Virology* 9:506-21 (1959).
Burrage et al., Structural differences between foot-and-mouth disease and poliomyelitis viruses influence their inactivation by aziridines, *Vaccine*, 18(22):2454-61 (2000).
Cavanagh, et al. Pneumovirus-like characteristics of the mRNA and proteins of turkey rhinotracheitis virus, *Virus Res.* 11:241-56 (1988).
Cline et al., Respiratory syncytial virus isolation by combined continuous flow-isopycnic bandind centrifugation, *J. Virol.* 1(4):659-64 (1967).
Dea et al., Antigenic variant of swine influenza virus causing proliferative and necrotizing pneumonia in pigs, *J. Vet. Diagn. Invest.* 4:380-92 (1992).
Dorin et al., Principles of continuous flow centrifugation, Technical Information, pp. 1-15 (2004).
English translations of Examination and Search Reports issued in connection with Taiwanese Patent Application No. 097116163, dated Dec. 21, 2012.
Floyd et al., Aggregation of poliovirus and reovirus by dilution in water, *Appl. Environ. Microbiol.* 33(1):159-67 (1977).
Gordon et al., Purification of maize dwarf mosaic virus by continuous-flow centrifugation, *Phytopathol.* 63:1386-92 (1973).
Grandgenett et al., Large-scale purification of ribonucleic acid tumor viruses by use of continuos-flow density gradient centrifugation, *Appl. Microbiol.* 26(3):452-4 (1973).
Harrap et al., The properties of three baculoviruses from closely related hosts, *Virology*, 79: 14-31 (1977).
International Search Report from PCT/EP2008/003531 dated Dec. 31, 2008.
Klingmuller et al., Hepadnavirus infection requires interaction between the viral pre-S domain and a specific hepatocellular receptor, *J. Virol.* 67(12): 7414-22 (1993).
Kretzschmar et al., Membrane association of influenza virus matrix protein does not require specific hydrophobic domains or the viral glycoproteins, *Virology*, 220:37-45 (1996).
McAleer et al., High-resolution flow-zone centrifuge system, *Biotechnol. Bioeng.* 21: 317-21 (1979).
Mistretta, et al., Purification and concentration of influenza inactivated viruses by continuous-flow zonal centrifugation, Bollettino Dell'Istituto Sieroterapico Milanese, Istituto Sierterapico Milanese, Milan, IT, 54(1):45-56 (1975).
Muys et al., Cellular transfer and AFM imaging of cancer cells using Bioimprint. *J. Nanobiotechnol.* 4: 1-11 (2006).
Poiesz et al., Detection and isolation of type C retrovirus particles from fresh and cultured lymphocytes of a patient with cutaneous T-cell lymphoma. *Proc. Natl. Acad. Sci. USA*, 77(12): 7415-9 (1980).
Putnak et al. Development of a purified, inactivated, Dengu-2 virus vaccine prototype in vero cells: Immunogenicity and protection in mice and rhesus monkeys. *J. Infect. Dis.* 174: 1176-84 (1996).
Pyke et al., Sucrose density gradient centrifugation and cross-flow filtration methods for the production of arbovirus antigens inactivated by binary ethylenimine, *BMC Microbiology*, 4(3):1-8 (2004).
Reimer et al., Purification of large quantities of influenza virus by density gradient centrifugation, *J. Virol.* 1(6): 1207-16 (1967).
Scholz et al. Acid stability of hepatitis A virus, *J. Gen. Virol.* 70:2481-5 (1989).
Trudel et al. Purification of infectious rubella virus by gel filtration on sepharose 2B compared to gradient centrifugation in sucrose, sodium metrizoate and metrizamide, *J. Virol. Meth.* 2:141-8 (1981).
Uyeda et al., Purification and serology of bean yellow mosaic virus, *Ann. Phytopath. Soc. Japan*, 41:192-203 (1975).
Zwerner et al., Harvesting the products of cell growth, *Meth. Enzymol.* 58: 221-9 (1979).
Imahori and Yamakawa, Seikagaku Jiten [Biochemistry Dictionary], Mar. 1, 2000, Third Ed., p. 161.
English Language Translation of Notice of Reasons for Rejection of Japanese Patent Application No. 2014-258342, dated Nov. 11, 2015.

\* cited by examiner

FORMULATION OF SUGAR SOLUTIONS FOR CONTINUOUS ULTRACENTRIFUGATION FOR VIRUS PURIFICATION

This application is a continuation of U.S. patent application Ser. No. 12/112,191 (now U.S. Pat. No. 8,969,533), filed Apr. 30, 2008, which claims the benefit of priority to U.S. Provisional Application No. 60/927,692, filed May 4, 2007, the contents of which are incorporated by reference in their entirety.

FIELD OF THE INVENTION

The present invention relates to the field of virus purification.

BACKGROUND OF THE INVENTION

Viruses, either those occurring in nature, or recombinant versions thereof, are used for vaccination and in the field of gene therapy. It is possible for many viruses or virus-like particles to safely and efficiently propagate in host cells. Several publications describe the purification of viruses from host cells, mostly concentrating on the use of specific chromatographic matrices for purification of the virus from a host cell lysate (see, e.g. U.S. Pat. No. 6,008,036). Other methods as described, for example, in U.S. Pat. No. 6,048,537 employ continuous sucrose gradient centrifugation, which delivers products with less antigen purity and requires further purification steps by centrifugation. Such methods also suffer from antigen aggregation, which can lead to a loss of viral antigen, or inhibit viral inactivation steps.

Viral aggregation can also inhibit the yield of chromatographic processes, which are time and cost intensive and difficult to adapt to a large scale production. It is therefore a goal of the present invention to provide a method to purify viruses, in particular from host cell samples, that is simple but still is capable of providing whole virus antigen fractions in high purity with reduced viral antigen aggregation.

SUMMARY OF THE INVENTION

Figure 1A:
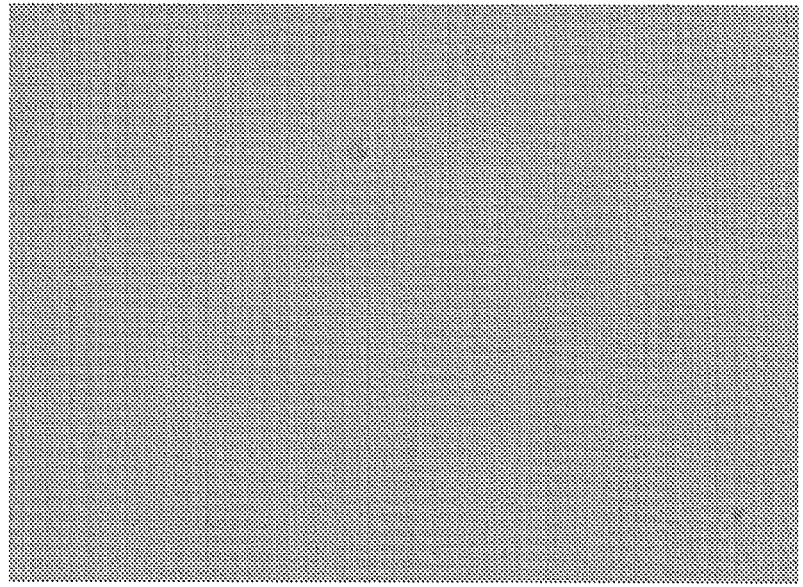
FIG. 1: Microphotograph of PMVHs purified with the conventional (FIG. 1a) and the inventive (FIG. 1b) ultracentrifugation procedures.

The present invention provides a method for purification of a virus or virus antigen comprising providing a virus preparation and centrifugation of said virus preparation in a gradient of a sugar established by a first layer A of the sugar in a concentration of a sucrose equivalent of 34% to 50% (w/w %) and a second layer B of the sugar in a concentration of a sucrose equivalent of 50% to 65% (w/w %) sucrose, in an aqueous buffer, with one buffer component being a buffer component having a pKa value between 6.0 and 9.4, and collecting said virus or virus antigen from the centrifugate, i.e. the product of the centrifugation process.

One aspect of the invention is to provide a method for purification of a virus or virus antigen. The method involves providing a solution containing a sugar gradient established by centrifuging at least a first buffered sugar solution and at least a second buffered sugar solution. The concentration of sugar in the first buffered sugar solution has a sucrose equivalent of 35% to 50% (w/w %), or in certain embodiments, 34% to 46% (w/w %). The concentration of sugar second buffered sugar solution has a sucrose equivalent of 50% to 65% (w/w %), or in certain embodiments, 50% to 60% (w/w %). Once the sugar gradient is established, a virus preparation is added to the sugar gradient. The virus preparation and sugar gradient are then centrifuged to obtain a peak pool, and the peak pool is extract to obtain the virus or virus antigen

DETAILED DESCRIPTION OF THE INVENTION

During purification of a virus or viral antigen, the virus or the viral antigen is concentrated by centrifugation, allowing a separation from cell culture media components and/or host cells and host cell components. The inventive method can minimize virus aggregation and virus loss at the centrifugation step of purification.

In the methods of the invention, a first sugar solution in a physiological buffer is loaded generally vertically into a continuous ultracentrifugation apparatus to form a horizontal sugar solution layer A, and then a second, higher concentration sugar solution in the same or different physiological buffer is loaded into the apparatus to form a horizontal sugar solution layer B. The apparatus is then activated, creating a sugar gradient that is most concentrated on outer wall of the apparatus, and that becomes less concentrated towards the center of the apparatus. A virus containing harvest solution from a cell culture is then loaded into the apparatus, and the virus particles migrate to a location in the sugar gradient where their density is equivalent to the density of the gradient. When the sugar is sucrose, a typical density range where this equilibration occurs is 36%-48% (w/w %) sucrose. Once the apparatus is halted, the gradient shifts to a horizontal position, and the portion of the gradient which contains the virus particles (or "peak pool") is withdrawn from the apparatus.

One aspect of this invention is the surprising discovery that by utilizing a two-layer solution approach, the volume of the peak pool can be increased as compared to conventional methods utilizing a single concentration of sucrose solution in water to form a sucrose gradient. This surprising effect is obtained even if sucrose is used and the maximum sucrose concentration in the gradient is the same as used in the conventional method. By optimizing the concentrations and amounts of the two sucrose solution layers A and B, the peak pool volume can be increased, for example, by twofold. This increased peak pool volume reduces the aggregation of whole virus particles, or antigen by reduction of their respective concentrations.

Continuous ultracentrifugation processes are useful for purification of virus preparations. Highly concentrated solutions of sugar (e.g., sucrose or sorbitol) or salt (e.g. $CsCl_2$ or NaBr) can be used to generate gradients by ultracentrifugation. However, sugar solutions without any additives have a low concentration of electrolytes and no buffer capacity. Thus, one aspect of the invention is the realization that virus preparations in sugar solutions, such as sucrose solutions, have a strong tendency to form aggregates, dependent on the concentration of the virus particles, which can cause problems in the further processing for vaccine production. The inventive methods can effectively minimize these problems using sugar solutions (e.g., sucrose solutions at 55% w/w) with the addition of salt at physiological concentrations (e.g., NaCl at about 4-8 g/kg) and with the addition of a buffer (e.g., Tris, approximately 10-20 mmol/kg, followed by pH adjustment) to achieve physiological electrolyte and pH conditions in the gradient. In certain embodiments, different sugar solutions are applied to build the gradient in the ultracentrifuge. As an example, 200 mL of a 55% w/w solution and 800 mL of a 42% w/w solution are loaded to the ultracentrifuge. The smaller amount of higher concentration sucrose solution ensures that at the end of the ultracentrifugation the maximum sucrose concentration remains above 45% and the larger amount of 42% sucrose results in a more gradual gradient in the range of about 40% where the virus peak maximum typically occurs. By these methods of the invention, the volume of the peak pool can be increased, and therefore the virus particle suspension is diluted and results in less aggregation. Also, the diffusion of molecules or particles between the supernatant which is loaded to the ultracentrifuge and the gradient is modified by using such sucrose formulations.

By way of example, a density gradient formed using approximately 42% and 55% (w/w %) sucrose solution in 20 mmol/kg Tris-buffer was found to be particularly useful for the influenza virus but can also be easily adapted for other viruses. Tris (trishydroxymethylaminomethane) is a useful buffer for pH ranges between 6.5 and 9.7. Although sucrose is used in this particular example of an embodiment of the invention, other sugars suitable for gradient centrifugation may be used. In addition, other buffer compounds, in particular organic buffer compounds, such as amines, can be used. Preferably the buffer has a pKa value above 6, 6.2, 6.4, 6.6, 6.8, 7.2, 7.4, 7.6, 7.8 or 8.0 and below 9.4, 9.2, 9.0, 8.8, 8.6, 8.4 or 8.2. Suitable buffers comprise for example HEPES (4-(2-hydroxyethyl)-1-piperazineethanesulfonic acid), ACES (N-(2-Acetamido)-2-aminoethanesulfonic acid), bis-tris-methane or -propane, CAPS (N-cyclohexyl-3-aminopropanesulfonic acid) or CAPSO, PIPES (piperazine-N,N'-bis(2-ethanesulfonic acid)), phosphate buffer, or any other buffer used in the field of biochemistry. The buffer is preferably chemically inert to biomolecules.

The centrifugation process can generate a peak pool fraction in which the virus particle is dispersed under physiological conditions with regard to electrolyte and pH conditions. The concentration of whole virus antigen in the peak pool fraction can be modified by adding different amounts of high and low concentration sugar solutions to define the gradient and therefore the volume of the peak fraction. Additionally, the volume of the peak fraction is also increased by the addition of salt and a suitable buffer (e.g. Tris-buffered saline (TBS)) alone, leading to a significantly higher yield of antigen and protein. This effect might be due to an unexpected improved mobility of proteins and virus antigen into a sugar gradient containing physiological concentrations of salt and a physiological pH. Different ultracentrifuge conditions (e.g., with and without preclarifier and different gravitational forces) clearly showed that a significant yield increase and a reduced aggregation of virus particles can be achieved by these modifications of the sucrose gradient.

Preferably the addition of electrolytes is greater than 50 mOsm/kg, 100 mOsm/kg, 150 mOsm/kg, 200 mOsm/kg or 250 mOsm/kg and less than 500 mOsm/kg, 450 mOsm/kg, 400 mOsm/kg or 350 mOsm/kg, preferably about 300 mOsm/kg. It should be noted that the amount of electrolyte is calculated as equivalent to the osmolality of aqueous solutions without the van't Hoffs factor correction. Moreover, the contribution of the gradient-forming substance (e.g., sucrose) is not used for the calculation. For example, the osmolality from electrolytes is calculated as follows: 8 g NaCl/kg/58.44 g/mol=136.9 mmol/kg×2 (ions/mol)=273.8 mOsm/kg+20 mM/kg TRIS×2 ions/mol=40 mOsm/kg; Total (NaCl+TRIS) 313.8 mOsm/kg). The pH value can be in physiological range, preferably between 5.5 and 9.5, more preferably between 5.5 and 8.5, especially preferred above 5.5, 6, 6.5 or 7 and below 9.5, 9.0, 8.5, 8 or 7.5, in particular between 7.0 and 7.5 or between 7.0 and 7.4.

In a particularly preferred embodiment, the sugar used to create a density gradient is sucrose. However, this invention also contemplates the use of other sugars, including alcohol sugars, a non-limiting example of which is sorbitol. Furthermore, the invention contemplates the use of hydrogenated sugars, linear sugars, modified sugars or any other sugar, provided that the sugar has a solubility in water sufficient to produce the solutions with the densities specified herein. Combinations of sugars (i.e., two or more sugars), either in the same or different layers, can also be used to generate the gradients described herein, provided that the corresponding sugar solutions that constitute those layers have the densities specified herein.

In preferred embodiments, the volume of the gradient forming preparation is between 5% to 100%, preferably above 5%, 10% 15%, 20%, 25%, 30%, 32%, 35%, 40%, 45% or 50% or less than 100%, 90%, 80%; 75%, 70%, 65%, 60%, 55%, 50%, 48%, 45%, 40%, 35%, 30% or 25%, of the effective volume of the ultracentrifugation rotor or device applying centrifugal forces to the sample. In other embodiments, the volume of gradient forming preparation is between 1% to 75% of the effective volume of the ultracentrifugation rotor or device applying centrifugal forces to the sample.

In preferred embodiments, the loading of the rotor containing the gradient forming material is carried out in a continuously or discontinuously repeated mode (i.e., either continuous ultracentrifugation or batch ultracentrifugation), where the loaded volume is preferably higher than the void volume of the rotor (total volume minus gradient volume), preferably more than 1×, 2×, 3×, 5×, 10×, 20×, 30×, 40×, 50×, 60×, 80× or less than 300×, 250×, 200×, 150×, 120×, 100×, 80×. In certain particularly preferred embodiments, continuous ultracentrifugation is used.

In a particularly preferred embodiment, the loaded volume is between 20 L to 50 L per 600 mL to 1000 mL void volume (1600 mL rotor volume minus 600 mL to 1000 mL void volume), which is about a 20× to 80× ratio. In another embodiment, the loaded volume is between 40 L to 100 L per 1200 mL to 2000 mL void volume (3200 mL rotor volume minus 1200 mL to2000 mL void volume, which is about a 20× to 80× ratio).

During centrifugation a continuous gradient of the sugar is established. In a further embodiment a fraction of the centrifugate is collected above a sucrose concentration of 24% (equivalent to about 1.10 kg/l), 26%, 28%, 30%, 32%, 34%, 36%, 38%, 40%, 42%, 44% or 46% (w/w %) (equivalent to about 1.22 kg/l) and less than 66% (equivalent to about 1.32 kg/l), 63%, 60%, 58%, 56%, 54%, 52%, 50%, 48%, 46% 44% or 42% (w/w %) (equivalent to about 1.19 kg/l). Normally, the viral product accumulates in this range. Preferably, a fraction of the centrifugate is collected between a sucrose concentration of about 30% and 54% (w/w %), more preferred between 36% and 48% (w/w %) sucrose. Fractions collected from gradients formed from other sugars might have different concentrations (w/w %), but equivalent densities. The densities of the collected fraction may be above 1.10 kg/l, 1.12 kg/l, 1.14 kg/l, 1.16 kg/l or 1.18 kg/l, 1.20 kg/l, 1.22 kg/l and below 1.32 kg/l, 1.30 kg/l, 1.28 kg/l, 1.26 kg/l, 1.24 kg/l, 1.22 kg/l or 1.20 kg/l. In particularly preferred embodiments, the densities may be between 1.13 and 1.25 kg/l, more preferred between 1.16 and 1.22 kg/l.

In certain embodiments, the concentration of buffer or buffer component (e.g., TRIS buffered saline) is in between 2 mmol/kg to 50 mmol/kg, preferably 5 mmol/kg to 40 mmol/kg, 10 mmol/kg to 40 mmol/kg, more preferably between 10 mmol/kg to 30 mmol/kg, more preferably between 18 mmol/kg to 25 mmol/kg, and is most preferred to be 20 mmol/kg. The buffer is preferably aqueous with less than 5% water-miscible organic solvents, more preferably less than 2% organic solvents, and is most preferably free of organic solvents. The buffer has a concentration of more than 2 mmol/kg, 5 mmol/kg, 10 mmol/kg, 12 mmol/kg, 14 mmol/kg, 15 mmol/kg, 17 mmol/kg, 18 mmol/kg, 19 mmol/kg or 20 mmol/kg or less than 50 mmol/kg, 40 mmol/kg, 35 mmol/kg, 30 mmol/kg, 25 mmol/kg, 23 mmol/kg or 21 mmol/kg.

The centrifugation can be performed preferably with a centrifugal force of at least 20,000 g, more preferably 30,000 g, more preferably 50,000 g, more preferably 70,000 g, most preferably 90,000 g, but in other embodiments, the centrifugal force is less than 200,000 g, less than 150,000 g, less than 120,000 g, less than 100,000 g, or less than 90,000 g.

In particular preferred embodiments, the volume ratio of the initial layer A to the initial layer B (i.e. before application of the virus preparation) is between 20:1 to 1:1, preferably between 10:1 to 1.5:1, more preferably between 8:1 to 2:1 even more preferably between 6:1 to 3:1, and most preferably 4:1. The ratio can be less than 20:1, 15:1, 10:1, 8:1, 5:1, 4:1, 3:1 or greater than 1:2, 1:1, 1.5:1, 2:1, 3:1 or 4:1.

In a particularly preferred embodiment, the sugar-containing centrifugation fluid is two-layered (i.e., comprising the sugar layers A and B of different concentrations prior to addition of the virus preparation, below the filler layer of liquid in the ultracentrifuge). Of course during centrifugation new concentration gradients or density gradients may form. However, this invention also contemplates centrifugation fluids with more than two layers. For example, in certain non-limiting embodiments, the centrifugation fluid is comprised of 3, 4, 5, 6, 7 or even 8 different layers. Each layer may have the same buffer as the other layers, or the buffers of each layer may be independently chosen.

In particularly preferred embodiments, the method of preparation does not comprise a preclarification step. However, if desired, preclarification may be carried out in a preclarification chamber of the ultracentrifugation apparatus.

In further embodiments layer A comprises between 40% to 44% (w/w %) sucrose, preferably from 41% to 43% (w/w %) sucrose. The sucrose concentration may be above 35% (equivalent to about 1.15 kg/l), 36%, 37%, 38%, 39%, 40%, 41% or 42% (w/w %) (equivalent to about 1.19 kg/l) or below 50% (equivalent to about 1.23 kg/l), 49%, 48%, 47%, 46%, 45%, 44%, 43% or 42% (w/w %) (equivalent to about 1.19 kg/l). Layer A formed from another sugar might have a different concentration on a weight/weight basis, but will have a density that falls within the density ranges specified herein.

In certain embodiments, layer B comprises a sucrose solution having a concentration between 50% to 65% (w/w %), preferably between 52% to 58% (w/w %), and more preferably between 54% to 56% (w/w %). The sucrose concentration (w/w %) may be above 50% (equivalent to about 1.23 kg/l), 51%, 52%, 53%, 54% or 55% (equivalent to about 1.26 kg/l) or below 66% (equivalent to about 1.32 kg/l), 64%, 62%, 61%, 60%, 59%, 58%, 57%, 56% or 55% (equivalent to about 1.26 kg/l). Layer B formed from other sugars might have a different concentration on a weight/weight basis, but will have a density that falls within the density ranges specified herein.

In a preferred embodiment of the present invention, the virus is an orthomyxovirus, in particular an influenza virus, preferably selected from influenza A and B. Non-limiting examples of other viruses contemplated by the invention include viruses selected from the group of RNA virus families such as Reoviridae, Picornaviridae, Caliciviridae, Togaviridae, Arenaviridae, Retroviridae, Flaviviridae, Orthomyxoviridae, Paramyxoviridae, Bunyaviridae, Rhabdoviridae, Filoviridae, Coronaviridae, Astroviridae, Bornaviridae, and DNA virus families such as Adenoviridae, Papovaviridae, Parvoviridae, Herpesviridae, Poxviridae, Hepadnaviridae. In certain preferred embodiments, the virus is selected from the group consisting of Influenza A/Panama/2007/99, A/New Caledonia/20/99, and B/Shangdong/7/97.

In some embodiments of the invention, the virus harvest is prepared from cells inoculated with the virus. The virus can be produced in any cells suitable for the production of viruses. Preferably, the cells are of an animal cell culture or cell line. Such cells may be from a specific tissue or embryonic cells such as embryonic eggs. The animal is preferably a mammal or a bird. In various embodiments of the invention, the cells are avian, canine, rodent, or primate cells. In specific embodiments, the cells are epithelial cells, in particular preferred kidney epithelial cells, such as Vero cells of an African green monkey.

The virus harvest applied to the ultracentrifugation apparatus may be the whole cell culture, or cell culture supernatant obtained after separating cells and/or portions thereof from the cell culture. In some embodiments of the invention, cells in the cell culture are allowed to settle in the culture vessel prior to drawing off a cell culture supernatant. In other embodiments of the invention, the cells may be lysed by chemical or mechanical methods, non-limiting examples of which include hypo or hypertonic lysis, detergent treatment, sonication, and mechanical disruption.

Preferably, the virus is inactivated or fragmented (e.g., as described in WO 05/11800) prior to or after the centrifugation. Additionally, a vaccine of the virus may be prepared by methods known in the art. A vaccine is an immunogenic composition of an antigenic substance, i.e. the (non-infections) virus, its hull, particles or its antigens, which an be used to immunize an animal, e.g. a mammal such as a human, or a bird.

The present invention is further illustrated by the following examples without being limited thereto.

EXAMPLES

During purification of influenza virus antigen, the monovalent harvest (MVH) is concentrated by ultracentrifugation. A continuous flow centrifugation procedure can be applied for the manufacture of the Vero cell culture grown viral vaccine based on a sucrose gradient formed using a 50% (w/w %) sucrose solution in water. The centrifuge rotor model used was equipped with a preclarifier. A number of fermentation optimization approaches like change of the Vero cell culture medium by supplementing soy hydrolysate or elevated temperature conditions in the early phase of Influenza virus replication resulted in a more robust process as well as increased antigen yields. Therefore it turned out that the 50% (w/w %) sucrose/water gradient did not allow to achieve the desired recovery due to limitations in the antigen binding capacity. In addition, the PMVHs (purified MVH) of virus strains New Caledonia, Panama and Shangdong showed unexpected antigen aggregation at this particular production step. Several attempts were made to minimize virus aggregation and virus loss at the centrifugation step. TRIS buffered saline instead of water was used to dissolve the sucrose for the gradient material. Furthermore the modification of using two gradient forming solutions with different densities was introduced to increase the peak pool volume. In addition, ultracentrifugation without preclarifier but with increased g-forces turned out to be a valuable tool for yield improvement. To prove this concept, results from previous purifications with standard (50% sucrose in water, with preclarifier at 20,000 rpm=90,000 g) and new conditions (42% and 55% sucrose (w/w %), 20 mmol/kg TRIS, 8 g/kg NaCl, without preclarifier at 35,000 rpm=90,000 g, with a harvest of PMVH from 48%-36% sucrose fraction) were evaluated.

sucrose/water system. A laboratory ultracentrifuge model RK-6 was used to purify 25 liter and 50 liter MVH aliquots under different conditions. An overview of the parameter setup and the results for purification runs with the sucrose/water and sucrose/TBS system is given in Table 1.

TABLE 1

Comparison of Influenza A/Panama/2007/99 antigen yield and PMVH appearance. Sucrose gradient purified virus from ultracentrifugation experiments with preclarifier at 30,000 g.

| Purification Run | Conditions/Setup | MVH Load (liter) | HA-SRD/protein ratio (mg/mg) | Peak Pool Volume (mL) | Antigen yield (mg antigen/liter harvest) | PMVH (appearance) |
|---|---|---|---|---|---|---|
| 1 | Sucrose/water 800 mL | 25 | 0.51 | 333 | 1.2 | aggregation |
| 2 | Sucrose/TBS 800 mL | 25 | 0.34 | 440 | 2.0 | reduced aggregation |
| 3 | Sucrose/TBS 800 mL | 50 | 0.26 | 492 | 1.4 | reduced aggregation |

From Table 1 it can be concluded that sucrose gradients in TBS have several advantages over the standard gradients in the sucrose/water system. For Purification Run 1 a yield of 1.2 mg antigen/L harvest could be achieved, the antigen fraction (PMVH) showed unexpected virus aggregation. The purification experiments (run 2) with sucrose in TBS gave increased antigen yields compared to reference run 1. For the TBS preparations a significant reduction in the aggregate fraction could be observed. Although the TBS sucrose gradient has several advantages over the standard system (sucrose/water), a loss in antigen yield was observed at higher loading (50 liters compared to 25 liters) of the gradient (run 3).

In both cases of using TBS instead of water, the peak pool volume increased, which is indicative for more diffusion between the loaded harvest and the gradient containing a buffer substance and other electrolytes.

Example 1

Materials and Methods

A continuous flow ultracentrifuge CC40S with a C40CTS rotor (rotor volume 1,600 mL) or an Alfa Wassermann ultracentrifuge RK6 with an equivalent rotor was used. Sucrose gradient solutions were loaded to the rotor and then accelerated to the rotational speed of 20,000 to 35,000 rpm. After continuous loading with the inactivated harvest, the rotor was flushed with buffer to remove residual protein, which had not entered the gradient. After flushing, the rotor was decelerated and the ultracentrifugation was stopped, allowing the gradient to shift from the radial to axial direction of the rotor. Elution and fractionation was carried according to sucrose concentrations. A Coriolis type density detection unit and a UV 254 nm detection unit were used to monitor the sucrose and protein concentration.

Samples of the purified inactivated harvests were measured for total protein concentration, HA-SRD and Vero Antigen by ELISA according to standardized procedures to quantify yield and purity from the ultracentrifugation experiments.

Example 2

Initial Experiments with a TBS-Sucrose Gradient

A number of small scale purification runs with A/Panama/2007/99 monovalent virus harvests indicated that the use of a sucrose gradient produced from a mixture of 50% w/w sucrose with 50% w/w Tris buffered saline (20 mmol/kg TRIS, 8 g/kg NaCl) (final concentration 10 mmol/kg TRIS, 4 g/kg NaCl) had several advantages over the standard Example 3

Development of a Two-Step Sucrose/TBS Gradient

This example shows an exemplary embodiment in which a sucrose gradient was modified to increase the volume of the peak pool fraction without changing the limits for fractionation. A sucrose gradient with a reduced concentration of 42% (w/w %) was used, which resulted in a less steep sucrose gradient eluted from the ultracentrifuge. In order to ensure a sufficiently high sucrose concentration in the gradient, a more concentrated sucrose/TBS solution of 50% (w/w %) was loaded subsequent to the 42% (w/w %) solution, which, as a higher concentration solution, formed a "cushion" to prevent from sedimentation of antigen on the wall of the rotor. Table 2 shows purification runs using such a two-step gradient with 900 mL of a less concentrated sucrose/TBS solution (42% w/w sucrose, 11.7 mmol/kg TRIS, 4.7 g/kg NaCl) and 100 mL of a more concentrated sucrose/TBS solution (50% w/w, 10 mmol/kg TRIS, 4 g/kg NaCl), compared to a purification run using a gradient formed only with a 50% sucrose/TBS solution, applied in different volumes (viz., 600, 800, and 1000 mL). The tests were performed with preclarifier at 20,000 rpm (RCF appr. 30,000 g).

By applying the different amounts and concentration of the sucrose/TBS solutions the yield and purity of the material were not influenced significantly. However, the use of the two-step gradient built up by the mixture of 42%/50% (w/w %) sucrose/TBS resulted in an significant increase of the peak pool volume, which leads to better purification conditions by reduction of the antigen concentration to avoid overloading of the peak pool fraction.

TABLE 2

Comparison of Product yield and Antigen purity of inactivated harvests of
A/Panama/2007/99 purified by ultracentrifugation with different amounts of Sucrose/TBS 50%
(w/w %) vs. a two Step Sucrose/TBS gradient (50%/42% (w/w %)).

| Purification Run | Conditions/ Setup | HA-SRD/protein ratio (mg/mg) | Antigen yield (mg antigen/liter harvest) | Peak Pool Volume (mL) |
|---|---|---|---|---|
| 1 | Sucrose/TBS 50% 600 mL | 0.58 | 1.3 | 346 |
| 2 | Sucrose/TBS 50% 800 mL | 0.58 | 1.3 | 325 |
| 3 | Sucrose/TBS 50% 1000 mL | 0.45 | 1.1 | 338 |
| 4 | Sucrose/TBS 42% 900 mL + Sucrose/TBS 50% 100 mL | 0.53 | 1.5 | 713 |

Example 4

Implementation of Higher Relative Centrifugal Forces without Preclarifier

Higher relative centrifugal forces for the ultracentrifugation were investigated to increase the antigen yield, however loss of material in the preclarifier had to be expected under such conditions. The ultracentrifugation rotors can be run with or without preclarifier, therfore a comparison of 20,000 rpm (appr. 30,000 g) with preclarifier and 35,000 rpm (appr. 90,000 g) in a two step sucrose/TBS gradient (100 mL of 50% w/w sucrose, final concentration 10 mmol/kg TRIS, 4 g/kg NaCl and 900 mL of 39% w/w sucrose, final concentration 12.2 mmol/kg TRIS, 4.9 g/kg NaCl) was carried out. In order to assess the potential loss of antigen, the preclarifier and the rotor wall were swabbed with buffer and analyzed for antigen losses. The results of this experiment are shown in Table 3. The antigen yield could be increased by over 60% from 1.7 mg HA-SRD/L harvest to 2.8 mg HA-SRD/L harvest. The main part of the missing antigen could be swabbed from the preclarifier, whereas only about 5% of the antigen was lost on the rotor wall of the ultracentrifuge. The SRD/Protein ratio is only slightly reduced by omitting the preclarification prior to loading the harvest onto the sucrose/TBS gradient.

TABLE 3

Comparison of product yield and losses and antigen purity by
ultracentrifugation of inactivated harvest of
A/Panama/2007/99 with different relative
centrifugal forces with and without preclarifier.

| Purification Run | Conditions/ Setup | HA-SRD/protein ratio (mg/mg) | Antigen yield (mg antigen/liter harvest) | Loss Rotor wall [mg SRD/L Harvest] | Loss in Preclarifier [mg SRD/L Harvest] |
|---|---|---|---|---|---|
| 1 | 20,000 rpm w/Preclarifier | 0.63 | 1.7 | 0.1 | 1.4 |
| 2 | 35,000 rpm w/o Preclarifier | 0.52 | 2.8 | 0.1 | N/A |

Example 5

Modification of the TRIS and NaCl Concentration in the Sucrose Gradients

Initial formulations were carried out by preparing a 50% w/w sucrose/TBS gradient by mixing of 50% (weight) sucrose to 50% (weight) TBS buffer (20 mmol/kg TRIS, 8 g/kg NaCl) resulting in final concentrations of 10 mmol/kg TRIS and 4 g/kg NaCl. Subsequently, less concentrated formulations 42%-39% sucrose/TBS solutions were prepared with higher amounts of TBS, resulting in lower concentrations of sucrose but correspondingly higher concentrations of TRIS and NaCl (see previous examples). More concentrated solutions like, for example, 55% (w/w/) sucrose in TBS had therefore lower concentrations of TRIS and NaCl.

In order to standardize the concentration of TRIS and NaCl in such preparations a new formulation was designed where 42%-55% weight sucrose was added to the mixing container, 20 mmol/kg (2.42 g/kg) TRIS and 8 g/kg NaCl were added and filled with water to 100% weight. Such preparations then had significantly (about 2x) higher concentrations of TRIS and NaCl compared to the formulations used in previous examples. Also refractometric measurements of such formulations resulted in about 2° (1°-3°) Brix higher refractometric results, due to the lesser amount of water, which was replaced by the addition of TRIS and NaCl before filling to the final weight of 100%.

In an experiment, two different versions of two-step sucrose/TBS gradients were compared. Gradients were built by adding 200 mT, of the higher concentrated sucrose/TBS solution to create a more robust, high density sucrose cushion in the gradient, after loading with 800 mL of 42% sucrose/TBS.

The results of the different sucrose/TBS preparations in an ultracentrifuge experiment are shown in Table 4. No significant differences could be observed with regard to yield or purity when different TRIS and NaCl concentrations were used.

TABLE 4

Comparison of Product yield and Antigen purity by Ultracentrifugation
of inactivated harvest of A/Panama/2007/99 with different Sucrose/
TBS preparations with different TRIS and NaCl concentrations.

| Purification Run | Conditions/ Setup | HA-SRD/protein ratio (mg/mg) | Antigen yield (mg antigen/liter harvest) |
|---|---|---|---|
| 1 | 42% sucrose in TBS (12.2 mmol/kg TRIS/ 4.9 g/kg NaCl) 55% sucrose in TBS (8.9 mmol/kg TRIS/ 3.6 g/kg NaCl) | 0.42 | 5.0 |
| 2 | 42% sucrose in TBS (20 mmol/kg TRIS/ 8 g/kg NaCl) 55% sucrose in TBS | 0.39 | 4.8 |

TABLE 4-continued

Comparison of Product yield and Antigen purity by Ultracentrifugation of inactivated harvest of A/Panama/2007/99 with different Sucrose/TBS preparations with different TRIS and NaCl concentrations.

| Purification Run | Conditions/ Setup | HA-SRD/protein ratio (mg/mg) | Antigen yield (mg antigen/liter harvest) |
|---|---|---|---|
| | (20 mmol/kg TRIS/ 8 g/kg NaCl) | | |

Example 6

Loading Capacity of the Rotor and Investigation of the Loading Flow Rate

Different harvest volumes of three different strains were investigated to assess the capacity of the optimized ultracentrifugation procedure and to investigate potential scale-up issues in manufacturing, when higher harvest volumes have to be applied to the ultracentrifugation procedure. Inactivated harvests were loaded with 15-17 L and 45-51 L on the 1600 mL rotor.

In this experiment, the same modified version of the two-step sucrose/TBS gradient was applied as in the previous example 5. First, the concentration of the higher density solution was increased to 55% w/w and a higher volume of 200 mL was used to create a more robust high density sucrose cushion in the gradient, after loading with 800 mL of 42% sucrose/TBS. Final TRIS concentration in the gradient was increased to 20 mmol/kg and the final NaCl concentration was increased to 8 g/kg in both sucrose/TBS solutions. Ultracentrifugation conditions were 35,000 rpm (90,000 g) without preclarifier, and fractionation was carried out between 48% to 36% sucrose.

The results of the loading capacity experiment are shown in Table 5.

With the inventive gradient and the higher centrifugation force without preclarifier only minor differences in yield of about 3% to 6% at different harvest loading volumes could be observed. This is in contrast to the limited loading capacity demonstrated in Example 2/Table 1, where for strain A/Panama/2007/99 an increase of the harvest volume from 25 liter to 50 liter resulted in a decrease in yield of about 30%. This improved yield can be explained by the combination of increased relative centrifugal forces and the improvement of the gradient profile and peak pool volume due to the two-step sucrose/TBS gradient.

TABLE 5

Comparison of Product yield and Antigen purity by Ultracentrifugation with different Loading Volumes.

| Purification Run | Strain/ Harvest Volume loaded | HA-SRD/protein ratio (mg/mg) | Antigen yield (mg antigen/liter harvest) |
|---|---|---|---|
| 1 | A/New Caledonia/20/99 45 liter | 0.37 | 1.6 |
| 2 | A/New Caledonia/20/99 15 liter | 0.45 | 1.7 |
| 3 | A/Panama/2007/99 51 liter | 0.36 | 1.9 |
| 4 | A/Panama/2007/99 17 liter | 0.44 | 2.0 |
| 5 | B/Shangdong/7/97 45 liter | 0.44 | 6.0 |
| 6 | B/Shangdong/7/97 15 liter | 0.51 | 6.2 |

Example 7

Comparison of the Inventive and Conventional Ultracentrifugation Procedures

The combined use of:

a) 90,000 g (35,000 rpm) without preclarifier (instead of 30,000 g (20,000 rpm) with preclarifier)

b) a sucrose gradient in TBS (instead of sucrose in water) with a final concentration of 20 mmol/kg TRIS and 8 g/kg NaCl c) forming such a gradient with two different sucrose concentrations (200 mL 55%+800 mL 42%) to increase the peak pool fraction volume (instead of 800 mL of 50% sucrose)

was compared with a previous, conventional ultracentrifugation procedure (Table 6).

TABLE 6

Conditions and setup of the manufacturing and small scale (1:2 scale down version) Purification unit operation at standard (50% sucrose in water) and new conditions.

| Method | Gradient | Sucrose | Virus Load (1/hr) | RPM | Fractionation |
|---|---|---|---|---|---|
| standard | Sucrose/ water | 800 mL 50% | 12.5 | 20.000 | acc. to UV signal (max. 50%-34%) |
| new | Sucrose/ TBS 20 mM | 800 mL 42% 200 mL 55% | 12.5 | 35.000* | 48%-36% |

*without preclarifier

Three comparative experiments were carried out with the 2002/2003 strains (viz., A/New Caledonia/20/99, A/Panama/2007/99 and B/Shangdong/7/97). The peak pool fractionation limits for these runs were defined with 48% to 36% (w/w %) sucrose. The results are shown in Example 8 to Example 10.

The results from purification runs with Influenza New Caledonia, Panama and Shangdong under standard (50% sucrose/water) and modified conditions (sucrose/TBS gradient) were compared on the basis of yield and product quality parameters.

Example 8

Purification of Influenza Strain A/New Caledonia/20/99

Purification experiments with conditions according to the standard procedure and the new sucrose/TBS gradient parameters according to Table 6 were carried out with New Caledonia MVH. In Table 7 a comparison of the results from purification runs is given.

TABLE 7

Comparison of A/New Caledonia/20/99 antigen yield, HA/protein ratio and Vero-protein impurity. Sucrose gradient purified virus with the conventional 2001/2002 method vs modified TBS gradient.

| Purification Run | Antigen yield (mg antigen/liter harvest) | HA/total protein ratio | Vero-protein/HA ratio |
|---|---|---|---|
| Standard | 2.7 | 0.41 | 0.06 |
| New (TBS gradient) | 3.4 | 0.60 | 0.07 |

Figure 1B:
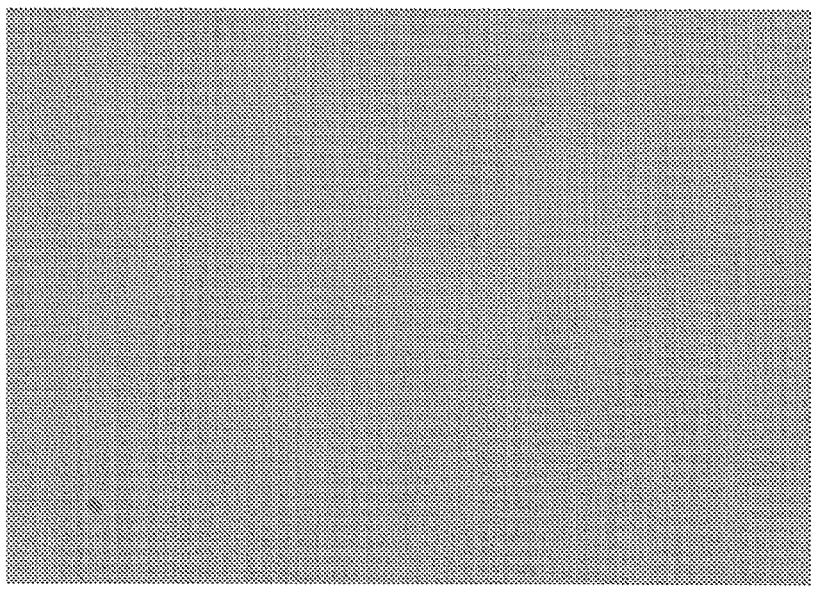

From the data in Table 7, it can be concluded that a significant process improvement was achieved with the new sucrose/TBS gradient purification conditions for Influenza strain A/New Caledonia/20/99. A significant increase in virus yield from 2.7 to 3.4 mg antigen per liter MVH was demonstrated for this particular strain. The virus antigen quality measured as HA/total protein ratio and Vero-protein/HA ratio shows that this increase in doses per liter did not compromise antigen quality. A slight increase in the HA/total protein from 0.41 to 0.60 was achieved with the new sucrose gradient conditions. For the host cell protein/HA ratio no significant difference could be detected. Under the sucrose/TBS gradient conditions for PMVH production, aggregation of strain A/New Caledonia/20/99 was slightly reduced. This effect could be confirmed by microscopic observation (see, e.g., FIG. 1A and FIG. 1B). At 400× magnification the stronger, formation of aggregates is clearly visible when applying the previous sucrose/water gradient version (FIG. 1A), whereas despite increased yields, the peak pool fraction derived from the optimized ultracentrifugation procedure appears to be significantly more homogenous (FIG. 1B).

Example 9

Purification of Influenza Strain A/Panama/2007/99

Purification experiments with conditions according to the standard procedure and the new sucrose/TBS gradient parameters according to Table 6 were carried out with Panama MVH. In Table 8 a comparison of the results from the purification runs is given.

TABLE 8

Comparison of A/Panama/2007/99 antigen yield, HA/protein ratio and Vero-protein impurity. Sucrose gradient purified virus with the standard method vs the inventive TBS gradient method.

| Purification Run | Antigen yield (mg antigen/liter harvest) | HA/total protein ratio | Vero-protein/HA ratio |
|---|---|---|---|
| standard | 2.0 | 1.47 | 0.06 |
| new (TBS gradient) | 5.5 | 0.77 | 0.07 |

From the data in Table 8 it can be concluded that a significant process improvement was achieved with the new sucrose/TBS gradient purification conditions for Influenza strain Panama. A significant increase in virus yield from 2.0 to 5.5 mg antigen per liter MVH was demonstrated for this particular strain by applying the new sucrose/TB S gradient conditions. A HA/total protein ratio of 0.77 was achieved, whereas for the PMVH produced under standard conditions the calculated ratio was 1.47. Due to the fact that no significant difference can be seen for the Vero-protein/HA ratio of PMVHs produced with both procedures, it is assumed that aggregation of the Panama antigen (as seen in a microphotograph comparison of Panama PMVHs (not shown)) may be the cause for the unusual HA/total protein ration of 1.47. For both purification procedures, the virus antigen quality measured as HA/total protein ratio and Vero-protein/HA ratio is acceptable. But, under the TBS sucrose gradient conditions for PMVH production, aggregation of strain Panama could be significantly reduced using the sucrose/TBS gradient.

Example 10

Purification of Strain B/Shangdong/7/97

Purification experiments with conditions according to the standard procedure and the new sucrose/TBS gradient parameters according to Table 6 were carried out with Shangdong MVH. In Table 9 a comparison of the results from purification runs is given.

TABLE 9

Comparison of B/Shangdong/7/97antigen yield, HA/protein ratio and Vero-protein impurity. Sucrose gradient purified virus with the standard method vs new TBS gradient method.

| Purification Run | Antigen yield (mg antigen/liter harvest) | HA/total protein ratio | Vero-protein/HA ratio |
|---|---|---|---|
| standard | 2.2 | 0.55 | 0.10 |
| new (TBS gradient) | 5.1 | 0.34 | 0.20 |

From the data in Table 9, it can be concluded that a significant process improvement was achieved with the inventive sucrose/TBS gradient purification conditions for Influenza strain B/Shangdong/7/97. A significant increase in virus yield from 2.2 to 5.1 mg antigen per liter MVH was demonstrated for this particular strain. The reduced HA/total protein ratio of 0.34 for the sucrose/TBS purified MVH lies within the specification range of the Influenza PMVHs. Further improvements of the B/Shangdong/7/97 virus replication phase allowed to establish a more consistent production process by changing the trypsin dosage profile. Under the TBS sucrose gradient conditions for PMVH production, aggregation of the B/Shangdong/7/97strain was significantly reduced as confirmed by a microphotograph (not shown) of Shangdong PMVHs purified with the standard versus TBS-conditions.

In the exemplary large and small scale experiments provided herein, it was demonstrated that the inventive sucrose gradient allows efficient loading of the monovalent harvests. There are many advantages of using the inventive methods described herein, including 1) increased virus yield of at least 25%, 2) a strain dependant HA/total protein ratio of 0.34 to 0.77, 3) a strain dependant host cell protein content of 2% to 7% and 4) minimized virus aggregation in the sucrose peak pool (PMVH).

What is claimed is:

1. A method for purifying a virus, comprising providing
   (i) a buffered sugar solution having a density of 1.15 kg/l to 1.23 kg/l and comprising a first physiological buffer and
   (ii) a buffered sugar solution having a density of 1.23 kg/l to 1.32 kg/l and which is higher than the buffered sugar solution (i), and comprising a physiological buffer which is the same or different from the physiological buffer of (i),
   wherein the volume ratio of buffered sugar solution (i) to buffered sugar solution (ii) is greater than or equal to 3:1;
   providing a virus preparation;
   centrifuging the virus preparation and buffered sugar solutions (i) and (ii) in a ultracentrifuge comprising an ultracentrifuge rotor to obtain a peak pool; and
   extracting the peak pool to obtain the virus.

2. The method of claim 1, wherein the volume of buffered sugar solutions (i) and (ii) is between 5% to 100% of the volume of the ultracentrifugation rotor.

3. The method of claim 1, wherein the peak pool has a density between 1.20 kg/l to 1.24 kg/l.

4. The method of claim 1, wherein one of said buffers has a concentration of between 5 mM to 50 mM.

5. The method of claim 4, wherein said buffer has a concentration of between 15 mM to 30 mM.

6. The method of claim 5, wherein said buffer has a concentration of between 18 mM to 25 mM.

7. The method of claim 1, wherein the step of centrifuging the virus preparation and buffered sugar solutions is performed with a relative centrifugation of at least 20,000 g.

8. The method of claim 7, wherein said relative centrifugation force is at least 30,000 g.

9. The method of claim 8, wherein said relative centrifugation force is at least 90,000 g.

10. The method of claim 1, wherein said volume ratio of said buffered sugar solution (i) to said buffered sugar solution (ii) is less than 20:1.

11. The method of claim 10, wherein said volume ratio is less than 10:1.

12. The method of claim 11, wherein said volume ratio is less than 8:1.

13. The method of claim 12, wherein said volume ratio is between 6:1 to 3:1.

14. The method of claim 1, wherein the virus preparation is obtained by centrifugation without a preclarifier.

15. The method of claim 1, wherein said virus preparation comprises cells inoculated with the virus.

16. The method of claim 15, wherein said cells are of an animal cell culture or cell line.

17. The method of claim 15, wherein said cells are epithelial cells.

18. The method of claim 17, wherein said cells are kidney epithelial cells.

19. The method of claim 18, wherein said cells are Vero cells.

20. The method of claim 1, wherein at least one of the physiological buffers is an amine buffer.

21. The method of claim 20, wherein at least one of the physiological buffers is a trishydroxymethylaminomethane (TRIS) buffer.

22. The method of claim 21, wherein the physiological buffer is TRIS-buffered saline.

23. The method of claim 1, wherein the volume of buffered sugar solutions (i) and (ii) is less than 100% of the volume of the ultracentrifuge rotor.

24. The method of claim 23, wherein the volume of buffered sugar solutions (i) and (ii) is less than 90% of the volume of the ultracentrifuge rotor.

25. The method of claim 1, wherein the volume of buffered sugar solutions (i) and (ii) is greater than or equal to 50% of the volume of the ultracentrifuge rotor.

26. The method of claim 24, wherein the volume of buffered sugar solutions (i) and (ii) is less than 90% of the volume of the ultracentrifuge rotor.

27. The method of claim 1, wherein the virus is a parvovirus.

* * * * *